(12) United States Patent
Dixon et al.

(10) Patent No.: US 10,366,594 B2
(45) Date of Patent: Jul. 30, 2019

(54) OIL AND GAS PRODUCTION FACILITY EMISSIONS SENSING AND ALERTING DEVICE, SYSTEM AND METHOD

(71) Applicant: Mountain Optech, Inc., Longmont, CO (US)

(72) Inventors: Mark Dixon, Gahanna, OH (US); Paul Brieser, Fort Collins, CO (US); Gregory P. Cenac, Estes Park, CO (US); David Burke, Rockledge, FL (US); Nick Cunningham, Longmont, CO (US); Bill McClintock, Boulder, CO (US)

(73) Assignee: Mountain Optech, Inc., Longmont, CO (US)

( * ) Notice: Subject to any disclaimer, the term of this patent is extended or adjusted under 35 U.S.C. 154(b) by 0 days.

(21) Appl. No.: 15/906,997

(22) Filed: Feb. 27, 2018

(65) Prior Publication Data

US 2018/0190101 A1 Jul. 5, 2018

Related U.S. Application Data

(63) Continuation-in-part of application No. 15/188,536, filed on Jun. 21, 2016, now abandoned, which is a (Continued)

(51) Int. Cl.
*G01N 1/22* (2006.01)
*E21B 43/26* (2006.01)
(Continued)

(52) U.S. Cl.
CPC .............. *G08B 21/12* (2013.01); *E21B 43/26* (2013.01); *G01M 15/104* (2013.01);
(Continued)

(58) Field of Classification Search
None
See application file for complete search history.

(56) References Cited

U.S. PATENT DOCUMENTS 3,699,814 A * 10/1972 Kaufman ................. G01N 1/24
 73/863.11
4,094,187 A * 6/1978 Navarre, Jr. ......... G01N 1/2258
 73/1.03

(Continued)

OTHER PUBLICATIONS

Libelium, "New Calibrated Air Quality Sensors for Smart Cities", "Retrieved from http://www.libelium.com/calibrated-air-quality-gas-dust-particle-matter-pm10-smart-cities", May 5, 2016, p. 6.

(Continued)

*Primary Examiner* — Fekadeselassie Girma
(74) *Attorney, Agent, or Firm* — Laura Schneider; Schneider IP Law LLC

(57) ABSTRACT

An emission detection system an enclosed combustion device stack is disclosed. The detection system has a sampling line having a first end exposed to a combusted gas passing through the stack exit port, to receive an undiluted gas sample from the stack exit port. The detection system has an electrostatic particulate matter sensor coupled to a second end of the sampling line, the second end positioned lower than and downstream of the first end, to analyze the undiluted gas sample. The detection system has an exhaust outlet coupled to and downstream of the electrostatic particulate matter sensor, to receive the undiluted gas sample from the electrostatic particulate matter sensor and feed the undiluted gas sample to the primary gas intake line upstream of the enclosed combustion device stack burner.

10 Claims, 7 Drawing Sheets

Related U.S. Application Data continuation of application No. 15/146,514, filed on May 4, 2016, now abandoned.

(60) Provisional application No. 62/156,595, filed on May 4, 2015.

(51) Int. Cl.
| | |
|---|---|
| G01M 15/10 | (2006.01) |
| G01N 15/00 | (2006.01) |
| G01N 15/06 | (2006.01) |
| G08B 17/10 | (2006.01) |
| G08B 21/12 | (2006.01) |

(52) U.S. Cl.
CPC ......... *G01N 1/2252* (2013.01); *G01N 1/2258* (2013.01); *G01N 15/06* (2013.01); *G01N 15/0656* (2013.01); *G08B 17/10* (2013.01); *G01N 2015/0046* (2013.01); *G01N 2015/0693* (2013.01)

(56) References Cited

U.S. PATENT DOCUMENTS

| | | | | |
|---|---|---|---|---|
| 4,591,414 A | * | 5/1986 | Zaromb | G01N 27/4045 204/406 |
| 4,660,408 A | * | 4/1987 | Lewis | G01M 15/102 73/28.06 |
| 4,738,147 A | * | 4/1988 | Tomlin | G01N 33/0011 55/490.1 |
| 4,883,505 A | * | 11/1989 | Lucero | G01N 1/2273 95/154 |
| 4,942,772 A | * | 7/1990 | Welker | G01N 1/2258 73/863.83 |
| 5,053,200 A | * | 10/1991 | Schaeffer | G01N 1/2258 138/42 |
| 5,065,579 A | * | 11/1991 | Monahan | F02G 1/045 60/524 |
| 5,143,695 A | * | 9/1992 | van den Burg | G01N 1/24 422/84 |
| 5,177,464 A | * | 1/1993 | Hamburg | F01N 11/00 340/438 |
| 5,184,501 A | * | 2/1993 | Lewis | G01N 1/2252 73/23.31 |
| 5,337,595 A | * | 8/1994 | Lewis | G01N 1/2252 73/23.31 |
| 5,355,672 A | * | 10/1994 | Adamczyk, Jr. | B01D 53/9481 60/274 |
| 5,408,215 A | * | 4/1995 | Hamburg | F01N 11/00 340/439 |
| 5,456,124 A | * | 10/1995 | Colvin | G01F 1/48 73/114.71 |
| 5,473,951 A | * | 12/1995 | Tomlin | G01N 1/2247 73/863.83 |
| 5,627,328 A | * | 5/1997 | Sheridan | G01N 1/2258 73/863.83 |
| H001757 H | * | 11/1998 | Seltzer | 73/863 |
| 6,327,889 B1 | * | 12/2001 | Seltzer | G01N 1/2258 356/243.2 |
| 6,627,155 B1 | * | 9/2003 | Uemura | G01N 31/12 250/288 |
| 6,644,962 B2 | * | 11/2003 | Sugimoto | C21D 1/52 432/128 |
| 6,973,818 B2 | * | 12/2005 | Silvis | G01M 15/102 73/1.02 |
| 7,263,823 B2 | * | 9/2007 | Andrews | F01N 3/0807 60/274 |
| 7,299,690 B2 | * | 11/2007 | Graze, Jr. | G01N 1/2252 73/114.42 |
| 7,395,725 B2 | * | 7/2008 | Shimizu | G01N 1/2202 73/863.12 |
| 7,560,013 B2 | * | 7/2009 | Shekarriz | G01N 27/4162 204/409 |
| 2004/0129564 A1 | * | 7/2004 | Kurachi | G01N 27/4071 204/424 |
| 2005/0072220 A1 | * | 4/2005 | Staphanos | G05B 23/0208 73/23.31 |
| 2005/0087028 A1 | * | 4/2005 | Widmer | G01N 1/2247 73/863.03 |
| 2005/0155410 A1 | * | 7/2005 | Manoosingh | G01N 29/022 73/31.01 |
| 2005/0160838 A1 | * | 7/2005 | Weaver | G01N 1/2247 73/863.03 |
| 2006/0288801 A1 | * | 12/2006 | Graze, Jr. | G01N 1/2252 73/863.02 |
| 2007/0111225 A1 | * | 5/2007 | Lambert | G01N 15/1459 435/6.18 |
| 2008/0282764 A1 | * | 11/2008 | Holt | G01N 33/0045 73/1.03 |
| 2009/0010828 A1 | * | 1/2009 | Holmes | B01D 53/64 423/210 |
| 2009/0230962 A1 | * | 9/2009 | White | G01N 24/08 324/317 |
| 2010/0058742 A1 | * | 3/2010 | Hirata | B01D 53/9454 60/286 |
| 2010/0208765 A1 | * | 8/2010 | Carlson | C21C 5/5211 373/9 |
| 2010/0258094 A1 | * | 10/2010 | Hull | F02B 51/04 123/536 |
| 2011/0094482 A1 | * | 4/2011 | Weber | F02B 47/08 123/568.12 |
| 2011/0146378 A1 | * | 6/2011 | Brand | G01N 1/2258 73/23.31 |
| 2011/0154891 A1 | * | 6/2011 | Yoshimura | F02D 41/0072 73/114.74 |
| 2011/0174053 A1 | * | 7/2011 | Holt | F01D 21/003 73/23.31 |
| 2011/0252864 A1 | * | 10/2011 | Guenther | G01N 1/2252 73/23.31 |
| 2012/0073433 A1 | * | 3/2012 | Woodson | B03C 3/68 95/3 |
| 2012/0210803 A1 | * | 8/2012 | Silvis | G01N 1/2252 73/863.02 |
| 2013/0150236 A1 | * | 6/2013 | Aoki | B01J 23/63 502/303 |
| 2014/0360702 A1 | * | 12/2014 | Cook | F23J 15/04 165/104.31 |
| 2015/0153254 A1 | * | 6/2015 | Silvis | G01M 15/10 73/864 |
| 2015/0338311 A1 | * | 11/2015 | Marek | G01N 1/2247 73/114.69 |
| 2016/0040573 A1 | * | 2/2016 | Aso | F01N 13/008 60/297 |
| 2016/0084181 A1 | * | 3/2016 | Henry | F02M 26/43 123/568.21 |
| 2016/0131013 A1 | * | 5/2016 | Yi | F01N 13/08 60/274 |
| 2016/0146142 A1 | * | 5/2016 | Harper | G01N 33/0036 123/703 |
| 2016/0160721 A1 | * | 6/2016 | Zhang | F01N 3/033 60/274 |
| 2016/0221044 A1 | * | 8/2016 | Linton | B08B 3/026 |
| 2017/0167348 A1 | * | 6/2017 | Yoshimura | F01N 3/00 |
| 2018/0113058 A1 | * | 4/2018 | Schroder | G01N 1/2252 |
| 2018/0172553 A1 | * | 6/2018 | Schuster | G01M 15/102 |

OTHER PUBLICATIONS

Girma, Fekadeselass, "Office Action U.S. Appl. No. 15/146,514", dated Aug. 25, 2016, p. 42 Published in: US.

Air-Vac, "316 Stainless Steel: HAVRSS & HAVSS Series", Retrieved from http://www.airvacpumps.com/AVstainless.html, May 3, 2015, p. 4.

Orange County/ Inland Empire SBDC Network, "EmiSense Success Story", Retrieved from https://www.youtube.com/watch?v=IICJv_yxqd0, Mar. 4, 2014, Published in: US.

Emisense Technologies, LLC, "Smart Sensors—Clean Emissions", Retrieved from http://emisense.com/, May 3, 2015, p. 1.

(56) References Cited

OTHER PUBLICATIONS

Jacobs Process Analytics, Inc., "Educators", Retrieved from http://jacobsanalytics.com/eductors/, May 3, 2015, p. 2.
Masoudi, et al., "Soot (PM) Sensors", Retrieved from https://www.dieselnet.com/tech/dpf_soot_sensors.php, 2014, p. 3.
Girma, Fekadeselass, "Office Action U.S. Appl. No. 15/188,536", dated Aug. 26, 2016, p. 22, Published in: US.
Pericval, Shane, "Response to Office Action U.S. Appl. No. 15/188,536", dated Nov. 28, 2016, p. 17, Published in: US.
Girma, Fekadeselass, "Office Action U.S. Appl. No. 15/188,536", dated Jan. 5, 2017, p. 31, Published in: US.
Schneider, Laura, "Response to Office Action U.S. Appl. No. 15/188,536", dated Apr. 4, 2017, p. 14, Published in: US.
Girma, Fekadeselass, "Office Action U.S. Appl. No. 15/188,536", dated May 4, 2017, p. 23, Published in: US.
Schneider, Laura, "Response to Office Action U.S. Appl. No. 15/188,536", dated Jul. 31, 2017, p. 11, Published in: US.
Girma, Fekadeselass, "Office Action U.S. Appl. No. 15/188,536", dated Aug. 29, 2017, p. 18, Published in: US.

\* cited by examiner

OIL AND GAS PRODUCTION FACILITY EMISSIONS SENSING AND ALERTING DEVICE, SYSTEM AND METHOD

PRIORITY

This application is a continuation in part of U.S. application Ser. No. 15/188,536 filed on Jun. 21, 2016 and entitled 'Oil and Gas Production Facility Emissions Sensing and Alerting Device, System, and Method' in continuation of U.S. application Ser. No. 15/146,514 filed on May 4, 2016 and entitled "Oil and Gas Production Facility Emissions Sensing and Alerting Device, System, and Method" which claims priority to U.S. Provisional Application No. 62/156,595 filed on May 4, 2015 and entitled "Oil and Gas Production Facility Emission Sensing and Alerting Device, System, and Method." All applications are incorporated herein by reference in their entirety.

FIELD OF THE DISCLOSURE

The present disclosure relates to the oil and gas industry. In particular, but not by way of limitation, the present disclosure relates to providing early detection of visible emissions from an oil and gas well enclosed combustion device ("ECD").

BACKGROUND OF THE INVENTION

Hydraulic fracturing ("frocking") is an oil and gas extraction technique that has seen an extraordinary increase in use during the last decade. Dining frocking, underground rock is fractured through the introduction of a highly-pressurized mixture of water, chemicals, and sand. The oil and gas within the rock is then released to the ground through the rock fractures. With the increased use of frocking methods to extract oil and gas, concern over how fracking affects the surrounding environment has increased as well. Such concern has led to federal, state, and local regulatory efforts to stein the release of emissions from production facility sites. For example, oil and gas operators may be fined for visible emissions, aka black smoke, emitted from an emission control device.

In the year 2015, the Environmental Protection Agency promulgated rules requiring routine visible inspection of flare sites for "visible emissions". Since that time, oil and gas companies have struggled to comply with these rules, due to the nature of the industry—namely, many well sites are located in remote, difficult-to-reach locations. Currently, the only visible emission detection process used by oil and gas operators comprises employing visual inspection of well sites.

Oil and gas companies need an efficient solution to monitor remote well sites, and other new and inventive improvements.

SUMMARY OF THE INVENTION

An exemplary emission detection system for an enclosed combustion device stack having a lower portion with an enclosed combustion device stack burner and a primary gas intake line, and an upper portion with a stack exit port is disclosed. The exemplary detection system has a sampling line having a first end exposed to a combusted gas passing through the stack exit port, the sampling line configured to receive an undiluted gas sample from the stack exit port. The exemplary detection system has an electrostatic particulate matter sensor coupled to a second end of the sampling line, the second end positioned lower than and downstream of the first end, the electrostatic particulate matter sensor positioned and configured to analyze the undiluted gas sample. The exemplary detection system has an exhaust outlet coupled to and downstream of the electrostatic particulate matter sensor, the exhaust outlet port configured to receive the undiluted gas sample from the electrostatic particulate matter sensor and feed the undiluted gas sample to the primary gas intake line upstream of the enclosed combustion device stack burner.

An exemplary method of retrofitting an enclosed combustion device stack with an emissions detection system is disclosed, for an enclosed combustion device stack having a lower portion with an enclosed combustion device stack burner and a primary gas intake line, and an upper portion with a stack exit port. The exemplary method includes exposing a first end of a sampling line to combusted gas passing through the stack exit port, the sampling line configured to receive an undiluted gas sample from the stack exit port. The exemplary method includes positioning a second end of the sampling line lower than the first end. The exemplary method includes coupling an electrostatic particulate matter sensor to the second end of the sampling line, the second end downstream of the first end, the electrostatic particulate matter sensor positioned and configured to analyze the undiluted gas sample. The exemplary method includes coupling a first end of an exhaust outlet to and downstream of the electrostatic particulate matter sensor, the exhaust outlet port configured to receive the undiluted gas sample from the electrostatic particulate matter sensor. The exemplary method includes coupling a second end of the exhaust outlet to the primary gas intake line upstream of the enclosed combustion device stack burner. The exemplary method includes feeding the undiluted gas sample to the primary gas intake line.

An exemplary oil or gas facility has an enclosed combustion device stack having a lower portion with an enclosed combustion device stack burner and a primary gas intake line, and an upper portion with a stack exit port. The exemplary facility has an emissions detection system. The emissions detection system has (a) a sampling line having a first exposed to a combusted gas passing through the stack exit port, the sampling line configured to receive an undiluted gas sample from the stack exit port; (b) a electrostatic particulate matter sensor coupled to a second end of the sampling line, the second end positioned lower than and downstream of the first end, the electrostatic particulate matter sensor positioned and configured to analyze the undiluted gas sample; and (c) an exhaust outlet coupled to and downstream of the electrostatic particulate matter sensor, the exhaust outlet port configured to receive the undiluted gas sample from the electrostatic particulate matter sensor and feed the undiluted gas sample to the primary gas intake line upstream of the enclosed combustion device stack burner.

BRIEF DESCRIPTION OF THE DRAWINGS

Various objects and advantages and a more complete understanding of the present invention are apparent and more readily appreciated by reference to the following Detailed Description and to the appended claims when taken in conjunction with the accompanying Drawings wherein:

DETAILED DESCRIPTION

Figure 1:
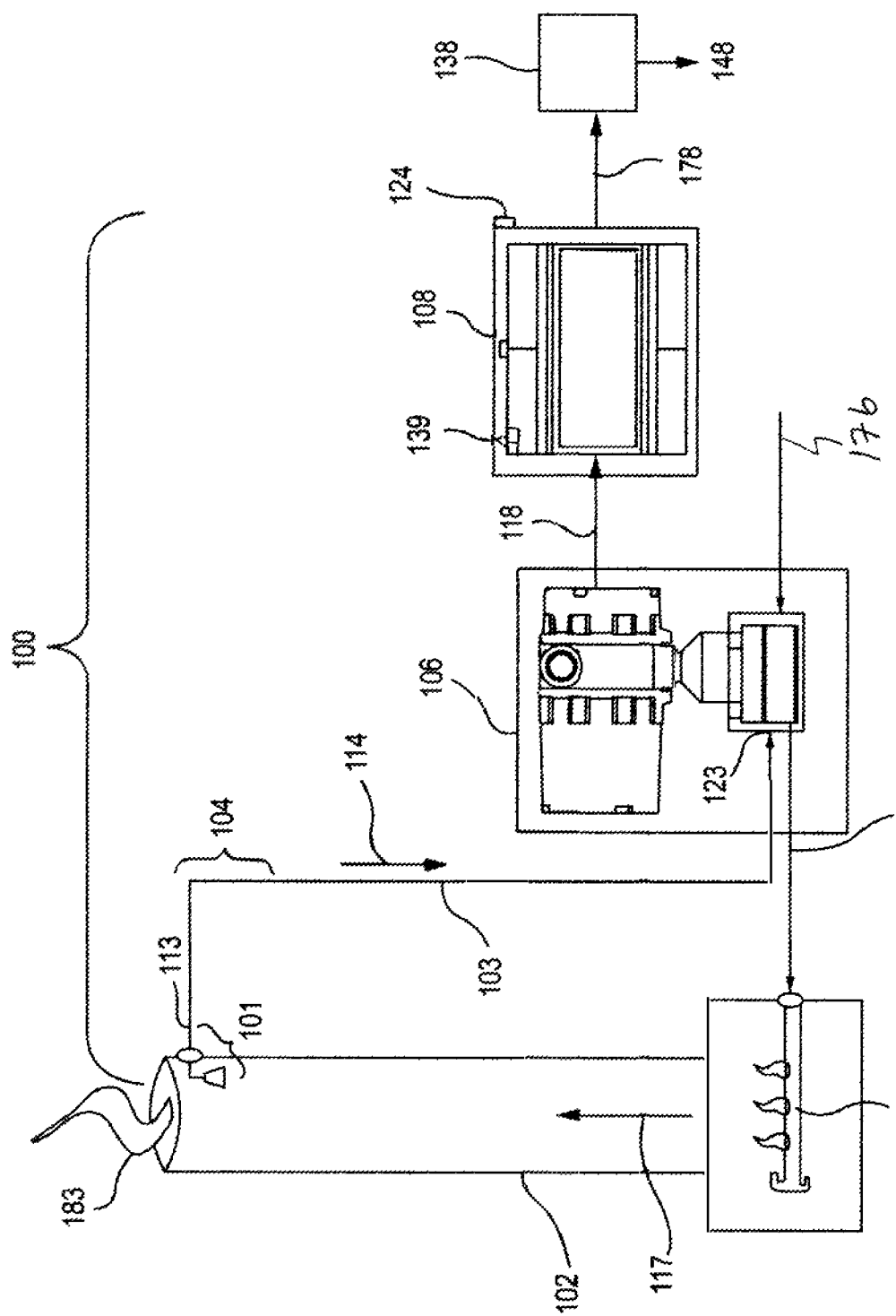
FIG. 1 depicts a diagrammatic representation of a sensing a reporting device according to one embodiment of the invention.

Before providing a more detailed description of the invention, it is expedient to provide an overview for a better understanding by the reader. As previously mentioned herein, oil and gas companies are straggling to comply with the Rules set forth by the EPA, including Method 22, which requires monitoring for visible emissions. In particular, oil and gas companies are faced with the daunting task of monitoring remote sites for visible emissions. Currently monitoring for visible emissions generally requires a human presence—either so that a person can physically monitor the site, or to maintain the equipment conducting the monitoring. Specifically, attempts to provide automatic or remote viewing are problematic for remote sites, because currently-available devices require significant maintenance, which demands a human presence. Additionally, even where a site is accessible by humans for direct monitoring, such direct monitoring is quite unreliable, due to how the visibility of emissions are affected by wind, temperature, humidity, and cloud conditions. Moreover, most remote sites were installed long before the EPA initiated the previously-mentioned Rules, such that retrofitting remote sites for remote monitoring is a separate daunting task.

It is also noted that some sensor technology is generally known from other fields, or, in sonic cases, is currently available, or could be available to the oil and gas industry. This sensor technology is generally not suited to solve the problems at hand.

For example, in optical sensors, a laser (visible or infrared) is projected across the expected smoke path or area. A receiver is placed at the end of the laser path or inside the transmitter housing, and smoke is detected when the laser path is interrupted, or the laser light is reflected back into the receiver. This technology works well indoors and in other industries but can be difficult to implement outdoors. For example, weather (e.g. high winds, extreme fog, or rain) or animals (birds) could cross the laser path and trigger a false positive resulting in unnecessary responses, a false negative resulting in environmental damage, and/or a need for more "smart" technology to eliminate false positives or false negatives. That is, the oil and gas companies are only looking for "visible emissions" which translates to black smoke only. White or translucent smoke (clouds, fog) would still trigger an optical sensor to some degree which is undesirable. Additionally, if an optical sensor was attached directly to the combustion chamber it would need to have a lens to see through, and the lens would become dirty with carbon after a black smoke event. This would require manual maintenance, defeating the purpose of remote monitoring.

In theory, the different gas byproducts of combustion could be sensed with various gas sensors (Oxygen, NOx, CO, etc.) to detect the combustion efficiency. These gas sensors work well in automotive applications, but do not translate well to oil and gas applications. First, these gas sensor cannot withstand the high temperatures of a well site, and the measurements can vary with temperature dramatically. Additionally, some gas sensors measurements drill over time, known as "zero span drift" so they need to be regularly recalibrated over time, defeating the purpose of remote monitoring. Most gas sensors can also be poisoned when exposed to high levels of hydrocarbons or other gases, such as carbon monoxide, which are present at very high levels in oil and gas systems, such that, at best, gas sensors would require significant maintenance or a dilution level that would introduce inaccuracies in the results.

Also, in theory, the sensor could be a "resistive accumulating" sensor. A resistive accumulating sensor, however, requires the buildup and burn-off of carbon directly on the sensor, with the problem resulting that other containments such as ash could build up on the sensor and lead to measurement drift and/or false positives.

The Applicant's device, as described herein, provides a means and method for autonomously monitoring well sites for visible emissions, so that the oil and gas companies can be quickly notified, so as to limit emissions having an environmental impact. A method of retrofitting is also described herein.

Turning first to FIG. 1, seen is one example of a sensing and reporting device 100. One such sensing and reporting device 100 may be located at an oil and/or gas facility and may be used to control emissions from storage tanks or other emission-producing systems. For example, as seen in FIG. 1, the sensing and reporting device 100 is coupled to, and adapted to monitor and provide an alert related to visible emissions emitted from a stack exit port 183 of an enclosed combustion device stack 102. The stack 102 may comprise an existing stack at an existing extraction site.

Figure 2:
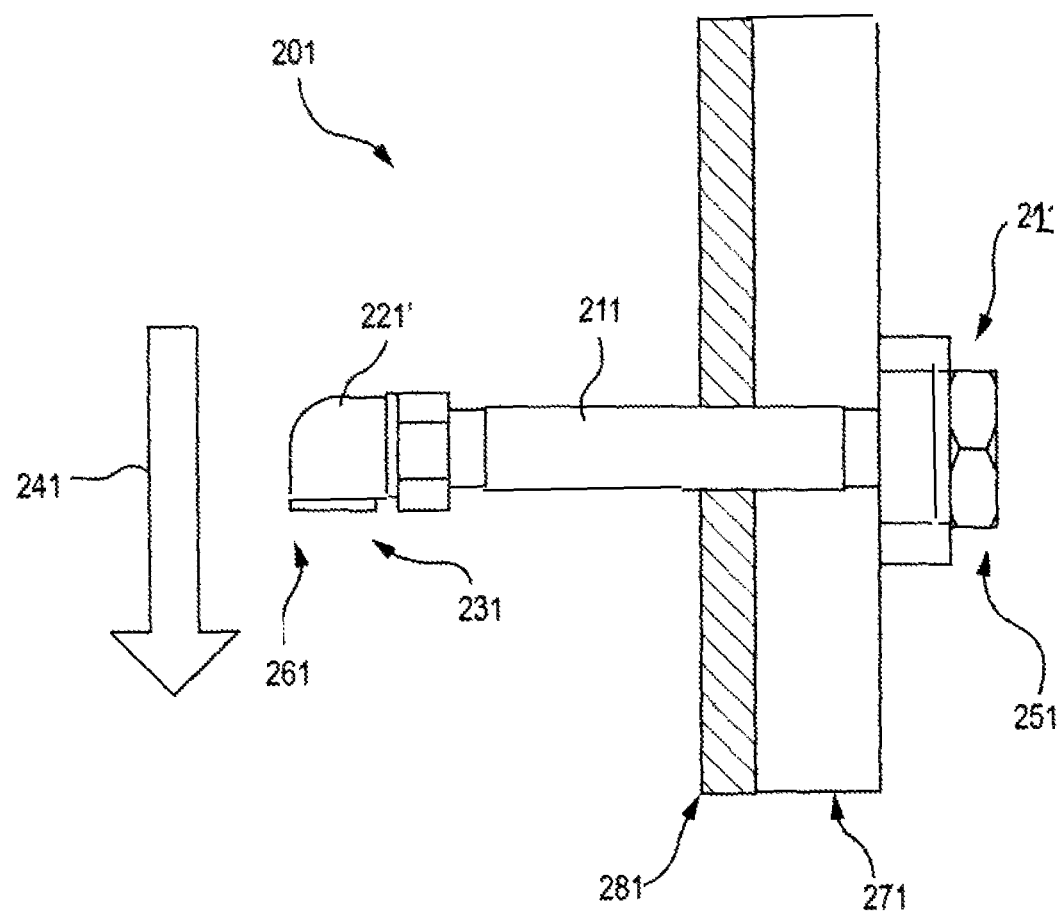
FIG. 2 depicts one example of an exhaust receiving section according to one embodiment of the invention.

The sensing and reporting device 100 in FIG. 1 comprises an exhaust receiving section 104, an exhaust analyzing instrument 106, and a control unit 108. The exhaust receiving section 104 comprises an exhaust intake port 101 and a sampling line 103. FIG. 2 shows a close up of one example of the, exhaust intake port 201. As seen e exhaust intake port 201 may comprise a pipe 211 and one or more pipe fittings 221 with a first of the one or more pipe fittings 221' comprising and opening 231 pointing in a direction 241 that ma comprise a direction 241 to towards the ground and/or towards an enclosed combustion device stack burner 107, as seen in FIG. 1. The pipe 211 and all other piping described herein may conform to NPT standards and may comprise sizes varying from 114" to 2" NPT. As seen in FIG. 2, the exhaust intake port 201 may extend from a first location 251 external to the ECD through a bore in the ECD sidewall 271 and insulation 281 to a second location 261 internal to the ECD. It is contemplated that the bore in the ECD sidewall 271 and insulation 281 may be located proximal to the stack exit port 183. As seen in FIG. 1, a first end 113 of the sampling line 103 may be coupled or integrated to the exhaust intake port 101, while a second end 123 may be coupled or integrated to the exhaust analyzing instrument 106. The term "coupled" and all similar terms as used herein refers to the connection of two separate and distinct objects, while the term "integrated" and all similar terms refers to a single, unitary object.

In some embodiments, the sampling line 103 is configured with a length that is sufficient to provide a temperature drop from the first end 113 to the second end so as to reduce the potential for a high temperature to damage the sensor 357, 466. In some embodiments, the length is selected to allow for evaporation of any condensation prior to the undiluted gas sample reaching the sensor 357, 466. In some embodiments, a catch pan (not illustrated) may be coupled to the sampling line 103 to capture condensation prior to the undiluted gas sample reaching the sensor 357, 466.

Figure 3A:
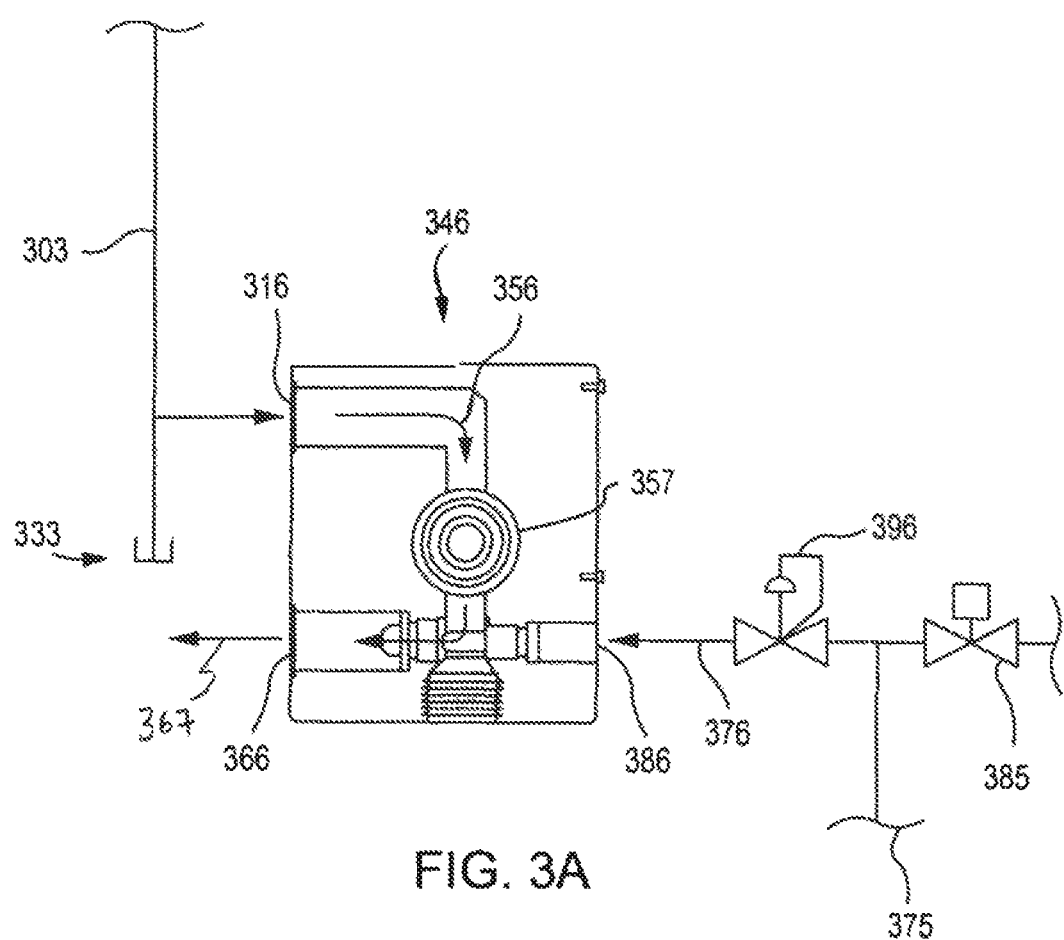
FIG. 3A depicts a diagrammatic representation of portions of a sensing a reporting device according to one embodiment of the invention.
Figure 4:
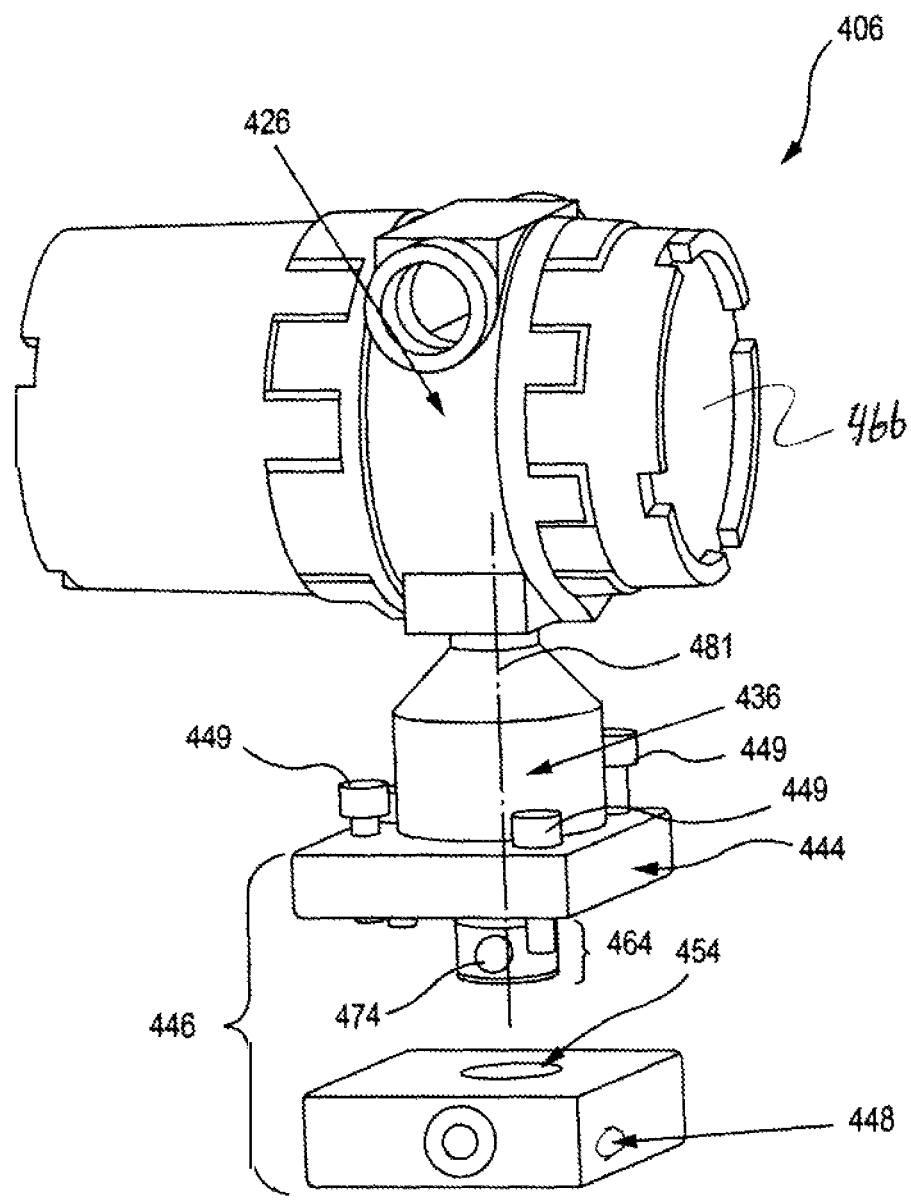
FIG. 4 depicts an exhaust sampling instrument according to one embodiment of the invention.

Turning now to FIG. 3A, seen is a portion of the sampling line 303 with a drip leg 333 and coupled to a sampling line inlet port 316 in a sampling block 346. As seen in FIG. 4, the sampling block 446 comprises a section of the exhaust analyzing instrument 406. For example, the exhaust analyzing instrument 406 may comprise an instrument housing 426, a probe chamber 436 coupled to the instrument housing 406 and a sampling block 446 coupled to the probe chamber 436. The sampling block 446 seen in FIG. 4 comprises a top section 444 and a bottom section 448. Coupled to and/or located within the housing 426 and/or probe chamber 436 may be one or more of the following sensors adapted to detect incomplete combustion or visible emissions within the exhaust sample received by the intake port 101 and sent to the instrument 406. Each of these sensors may implement an electrostatic charge sensing particulate measuring principle. However, other sensing types are also contemplated such as, but not limited to, accumulating electrode, radio frequency diffusion, through-beam, reflective, diffuse and optical sensing mechanisms. The sensors that may be implemented are particulate matter sensors a/k/a soot sensors; gas sensors for detecting carbon monoxide (CO), carbon dioxide (CO2), nitrogen oxides (NO, NO2, NO3, etc.), hydrogen (H), methane (CH4), and/or Oxygen (O2); electro-optical or photoelectric sensors to detect black particulate matter in smoke, visible or infrared sensors; carbon detection sensors; and/or a generic hydrocarbon gas sensor (CxHx). In one embodiment, it is contemplated that a housing terminal side 426 faces the same direction as the primary gas inlet 386.

In some embodiments, the probe chamber 436 or housing 426 may house a particulate matter sensor 466 (see also particulate matter sensor 357 in FIG. 3A. The particulate matter sensor may be configured to detect and/or carbon in the sample. Particulate matter sensors tend to be the most rugged with respect to high temperatures. In some embodiments, the particulate matter sensor may be an electrostatic particulate matter sensor. The electrostatic particulate matter sensor 466 may be configured to detect the carbon molecule between two electrodes. The electrostatic particulate matter sensor 466 may be an EmiSense PMTrac sensor, which was developed for the automobile industry.

Figure 3B:
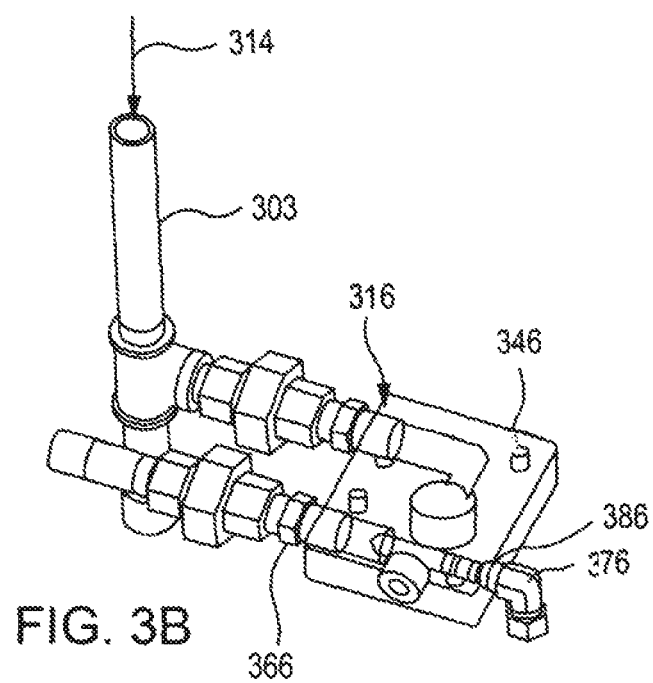
FIG. 3B depicts portions of a sensing a reporting device according to one embodiment of the invention.

Returning now to FIGS. 1-3A and as also seen in FIG. 3B, as the exhaust from the burner 107 travels 117 up the stack 102, the exhaust enters the opening 231 and moves 114, 314 towards the inlet port 316. Upon entering the sampling block 346, the exhaust flows 356 towards the probe chamber 436 or sensor 357, with a portion 464 of the probe chamber 436 being inserted and located in a sampling block bore 454. As the exhaust proceeds through a probe chamber bore 474, the exhaust analyzing instrument 406 detects a particulate matter level in the exhaust. It is contemplated that the exhaust analyzing instrument 406 may continuously sample the exhaust gas, for example, obtaining a measurement about every second. However, greater or lesser measurement amounts are contemplated—such as, but not limited to, one measurement every .01 s or one measurement every minute. As the exhaust exits the probe chamber bore 474, the exhaust continues towards, and exits the sampling block 346 through, an exhaust outlet 366. As seen in FIG. 1, the exhaust may proceed 177 to the enclosed combustion device stack 102 and enter the stack 102 proximal the enclosed combustion device stack burner 107. The exhaust may exit the sampling block 346 through piping 367 coupled to the exhaust outlet 366. It is contemplated that the probe chamber 436 may couple to a top section 144 of the sampling block 446 by, for example, a threaded coupling mechanism. The top section 444 may couple to the, bottom section 448 by one or more threaded bolts 449 coupled to threaded bores in the top section 444 and the bottom section 448. As seen in FIG, 4, the probe chamber 436 may also comprise a longitudinal axis 481. It is contemplated that the for axis 481 is generally vertically-aligned during operation of the instrument 406 and that the instrument housing 426 is located at a vertically-higher location than the probe chamber 436, as seen in FIG. 4.

Returning now to FIGS. 3A and 3B, as seen a gas line 376 is coupled to a primary gas inlet 386 on the sampling block 346. Upstream from the sampling block 346, a pressure regulator 396 is coupled to the gas line 376 downstream of a pilot light 375 and a solenoid valve 385. The pressure regulator 396 is set so that the gas line 376 pressure enables the flow 356 of the exhaust from the exhaust intake port 201, through the sampling block 346 and to the enclosed combustion device stack 102. Gas line 376 pressure is preferably set from about 15 psi to about 60 psi, more preferably set from about 17.5 psi to about 35 psi and most preferably set from about 20 psi to about 25 psi. The gas line 376 may comprise 1¼" NPT in one embodiment, with the sampling line 103 and exhaust piping 367 comprising 1h" NPT. Upon entering the sampling block 346, the gas will also exit the sampling block 346 through the exhaust outlet 366 to the stack 102.

In some embodiments, the sensor 357, 466 is intentionally positioned to promote flow of the undiluted sample. Specifically, the sensor 357, 466 is positioned lower than, and distal from, the stack exit port 183, so as to promote flow in a passive manner using a pressure differential between the combusted gas entering the sampling line 103 and the primary gas entering the combustion chamber. Because the sample is mixed with the primary gas after analysis, the pressure differential promotes flow between the two points. Additionally, a temperature differential between the two positions may be provided, further improving flow of the sample in a passive manner.

Returning now to FIG. 1, as the exhaust is monitored by the exhaust analyzing instrument 106, the exhaust analyzing instrument 106 may provide a signal to the control unit 108. One such control unit 108 may be adapted to receive a signal from ten separate exhaust analyzing instruments 106. In one embodiment, the exhaust analyzing instrument 106 may provide a first signal 118 to the control unit 108 when the exhaust analyzing instrument 106 has determined that the exhaust comprises a specified amount of visible emissions (i.e., black smoke) above a threshold level. For example, the first signal 118, that is continuously emitted front the instrument 106 to the control unit 108, may comprise a less than 5 nA (nanoAmp) sipial while the instrument fails to detect visible emissions. However, if visible emissions are detected, the first signal 118 may increase to about a 5 nA signal, or greater. In on embodiment, the 5 nA signal maybe emitted when the instrument determines that there is about 1-2 mg of soot per m 3 of exhaust. However, other values are contemplated. The black smoke may comprise soot due to incomplete combustion in the enclosed combustion device stack 102. The first signal 118 may comprise first information and may be received by a signal receiving portion of the control unit 108 such as, but not limited to, a two-wire communication system, one wire comprising a positive (+) communication and one wire comprising a negative (−) communication. Therefore, to receive communications from a plurality of instruments 106, the control system 108 may comprise a plurality of communication port pairs 139. Other communication types are contemplated. Upon receiving the first signal 118 from the exhaust analyzing instrument 106, the control unit 108 may output a second signal 128. One second signal 128 may inform one or more automation systems 138 of the emission level in the exhaust. The second signal 128 may be emitted from a signal emitting portion of the control unit 108 and may comprise second information related to the first information. One such signal emitting portion may comprise a MODBUS RTU 2-wire, RS-485 output. However, like the first signal 118, other second signal 128 types known in the art are contemplated. In one embodiment, the second signal 128 may only be emitted when the first signal comprises 5 nA or greater. In alternative embodiments, like the first signal 118, the second signal 128 may be continuously emitted and may comprise a value that initiates an alert 148 when the second signal value comprises a threshold value. For example, the alert 148 may be sent when the second signal 128 comprises a 5 mA, or greater, signal It is also contemplated that the automation system 138 and control unit 108 may comprise a single device. The automation system 138 may be configured to provide a real-time alert 148 regarding the visible emission level in the exhaust. For example, the automation system 138 may provide an email message to one or more designated email addresses or a text message to one or more designated telephone numbers. Other alerts 148 known in the art are also contemplated. Such alerts may enable oil and gas operators to avoid visible emission regulatory actions such as, but not limited to, fines. It is further contemplated that the control unit 108 may comprise a power receiving port 124 for receiving power from an external source.

With, again, reference to FIGS. 3A and 3B, the sample is acquired by a suction or vacuum, which is generated by creating high pressure at the gas inlet 386 and low pressure at exhaust outlet 366 which in turn causes negative pressure at inlet port 316 and therefore all through sampling line 103 up to opening 231 where the system releases to atmosphere. An important distinction is that the suction or vacuum effect is generated passively meaning that there are no moving parts or electronics that are subject to wear and tear or breaking down in remote locations. The system described herein is therefore less complex that currently-available options, but provides the end user with a consistent sample gas flow across, the sensing device 105. While those skilled in unrelated arts may recognize this as aspirator effect technology, it is noted that this has not well known in the oil and gas industry in the past.

It is also noted herein that the system described does not mix the sample gas with the primary gas. That is, the primary gas at gas inlet 386 is decoupled (separate) from the volume of gas sampled at the exhaust flow 356. This decoupling eliminates the need for a computerized calculation of dilution rates, and also improves the accuracy of the emissions detection, because any inaccuracy in the dilution rate would affect the accuracy of the emissions detection to a higher degree. The decoupling also eliminates the need for a separate supply of dilution air (e.g., compressed air), which improves the ability for oil and gas companies to retrofit their systems.

In some embodiments, the system mixes the sample gas and primary gas together downstream of the sensing element or chamber 436 at exhaust outlet 366 and piping 367. This mixture is then directed back into the main system upstream of the combustion chamber 107. Returning the mixture in this manner allows the ability to burn off the primary gas, which was the original intention for the gas. This return differs from all currently-available systems, which vent the sample back into the exhaust chamber or atmosphere.

It is contemplated that the alert 148 may only be issued after the second signal 128 informs the automation system 138 that the instrument 106 has found that visible emissions in the exhaust after a specified period of time. For example, a delay of four minutes may be set in the automation system 138 prior to issuing the alert 148 in order to prevent an alert 148 being issued based on an inaccurate reading. Greater or lesser delays such as, but not limited to, a delay of ten minutes or a delay of one minute may be implemented.

Figure 5:
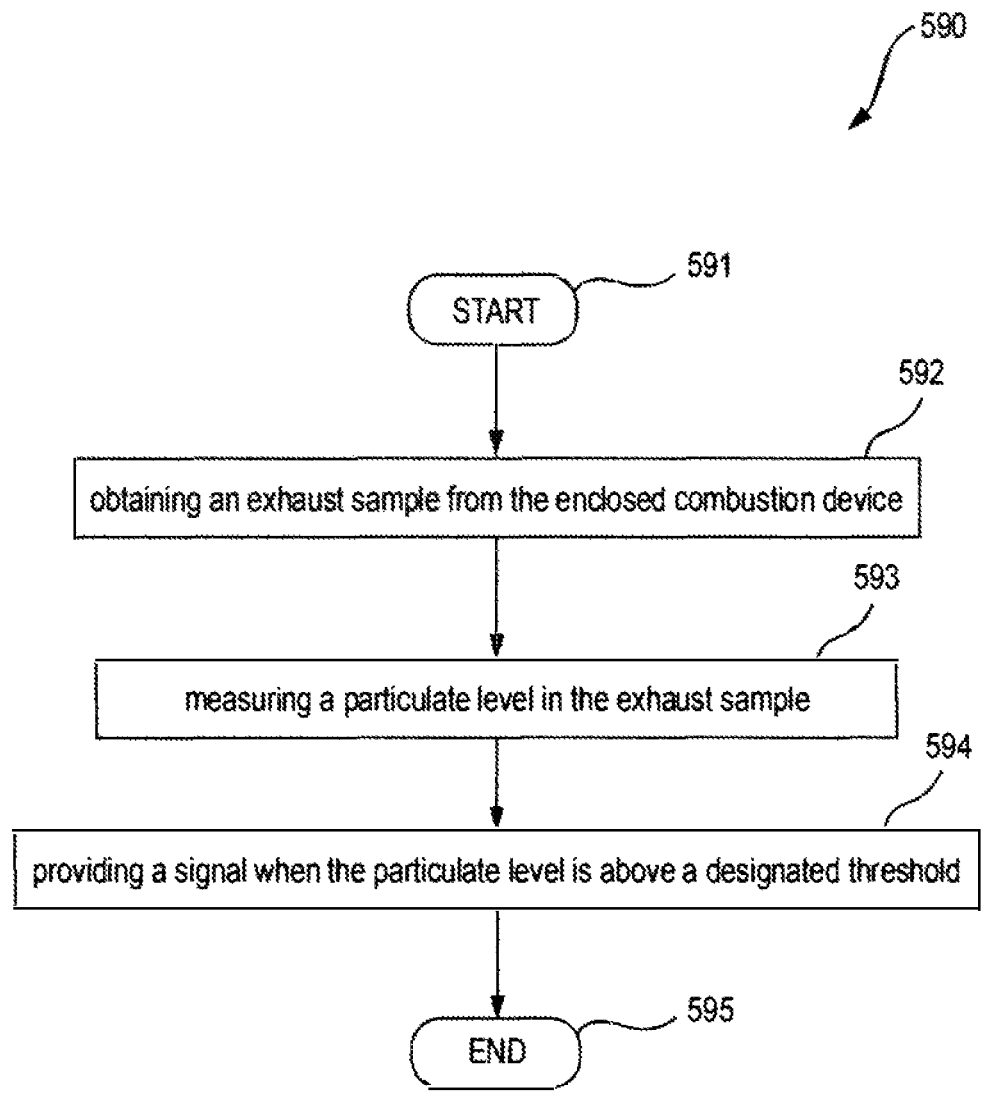
FIG. 5 depicts a method of obtaining a visible emission alert associated with an enclosed combustion device according to one embodiment of the invention.

Turning now to FIG. 5, seen is one method 590 of obtaining a visible emission alert associated with an enclosed combustion device such as, but not limited to, the alert 148 and enclosed combustion device stack 102 described with reference to FIGS. 1-4. The method starts at 591 and at 592 comprises obtaining an exhaust sample from the enclosed combustion device. For example the exhaust sample may be obtained by employing the system described with reference to FIGS. 1-4. At 593 the method 590 comprises measuring a particulate level in the exhaust sample such as, by rising the system described with reference to FIGS. 1-4. At step 594 the method 590 comprises providing a signal when the particulate level is above a designated threshold. For example, the first signal 118 and/or second signal 128 may be provided.

Although not seen in FIG. 5, in one method 590, obtaining an exhaust sample from the enclosed combustion device may comprise receiving the exhaust sample into an opening 231 of a pipe 211 with the opening 231 being located proximal the stack exit port 183. Additionally, measuring a particulate level in the exhaust sample may comprise connectively coupling the exhaust analyzing instrument 106 to the pipe 211 (e.g., through the sampling line 103) and coupling the gas line 176 to the exhaust analyzing instrument 106. The gas line pressure may be set through the pressure regulator 396 so that the gas line pressure creates a pressure difference between the pipe 211 and the exhaust analyzing instrument 106, and that pressure difference may enable the exhaust sample to flow to the exhaust analyzing instrument 106. Additional method 590 steps not shown in FIG. 5 may comprise exiting the exhaust sample and gas from the exhaust analyzing instrument 106 to the enclosed combustion device proximal an enclosed combustion device burner 107, for example, through piping 367 seen in FIG. 3.

Figure 6:
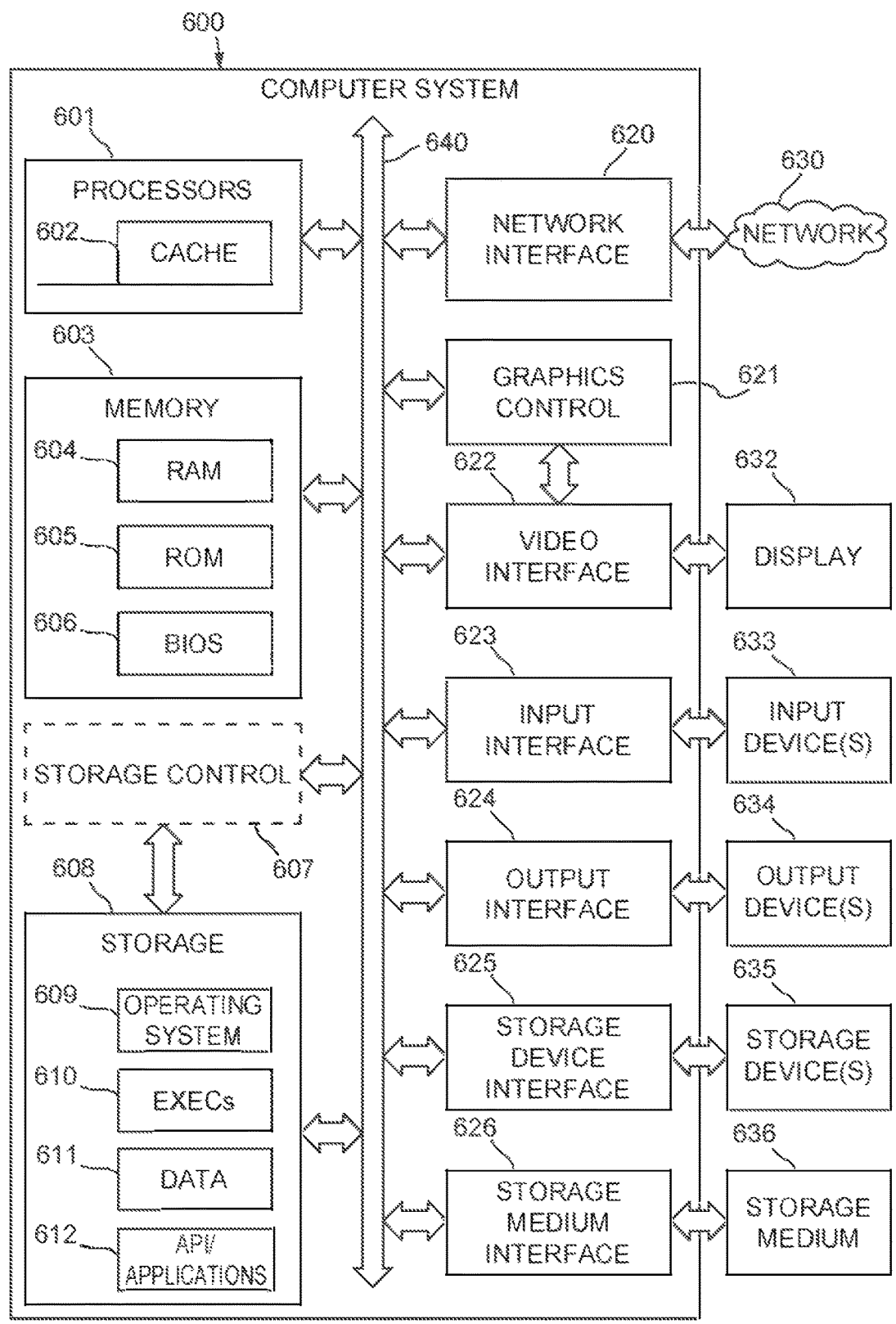
FIG. 6 depicts a diagrammatic representation of one embodiment of a computer system according to one embodiment of the invention.

The readings from the instrument may be stored, analyzed, and modified in the automation system 138. The computing devices described herein may also be referred to as a computing system or a computer system. For example, FIG. 6 shows a diagrammatic representation of one embodiment of a computer system 600 within which a set of instructions can be executed to cause a device to store such readings and/or perform or execute any one or more of the aspects and/or methodologies of the present disclosure. The components in FIG. 6 are examples only and do not limit the scope of use or functionality of any hardware, software, firmware, embedded logic component, or a combination of two or more such components implementing particular embodiments of this disclosure. Sonic or all of the illustrated components can be part of the computer system 600. For instance, the computer system 600 can be a general purpose computer (e.g., a laptop computer) or an embedded logic device (e.g., an FPGA), to name just two non-limiting examples.

Computer system 600 includes at least one processor 601 such as a central processing unit (CPU) or an FPGA to name two non-limiting examples. Any of the subsystems described throughout this disclosure could embody the processor 601. The computer system 600 may also comprise a memory 603 and a storage 608, both communicating with each other and with other components, via a bus 640. The bus 640 n also link a display 632, one or more input devices 633 (which may, for example, include a keypad, a keyboard, a mouse, a stylus, touch screen, etc.), one or more output devices 634, one or more storage devices 635, and various non-transitory, tangible computer-readable storage medial medium 636 with each other and with one or more of the processor 601, the memory 603, and the storage 608. All of these elements may interface directly or via one or more interfaces or adaptors to the bus 640. For instance, the various non-transitory, tangible computer-readable storage media 636 can interface with the bus 640 via storage medium interface 626. Computer system 600 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Processor(s) 601 (or central processing unit(s) (CPU(s))) optionally contains a cache memory unit 602 for temporary local storage of instructions, data, or computer addresses. Processor(s) 601 are configured to assist in execution of computer-readable instructions stored on at least one non-transitory, tangible computer-readable storage medium. Computer system 600 may provide functionality as a result of the processor(s) 601 executing software embodied in one or more non-transitory, tangible computer-readable storage media, such as memory 603, storage 608, storage devices 635, and/or storage medium 636 (e.g., read only memory (ROM)). For instance, instructions associated with at least a portion of the method 590 shown in FIG. 5 may be embodied in one or more non-transitory, tangible computer-readable storage media. The non-transitory, tangible computer-readable storage media (or medium) may store software comprising instructions that implements particular embodiments and processor(s) 601 may execute the software. Memory 603 may read the software from one or more other non-transitory, tangible computer-readable storage media (such as mass storage device(s) 635, 636) or from one or more other sources through a suitable interface, such as network interface 620. Any of the subsystems herein disclosed could include a network interface such as the network interface 620.

The software may cause processor(s) 601 to carry out one or more processes or one or more steps of one or more processes described or illustrated herein. Carrying out such processes or steps may include defining data structures stored in memory 603 and modifying the data structures as directed by the software. In some embodiments, an FPGA can store instructions for carrying out functionality as described in this disclosure. In other embodiments, firmware includes instructions for carrying out functionality as described in this disclosure.

The memory 603 may include various components (e.g., non-transitory, tangible computer-readable storage media) including, but not limited to, a random access memory component (e.g., RAM 604) (e.g., a static RAM "SRAM", a dynamic RAM "DRAM, etc.), a read-only component (e.g., ROM 605), and any combinations thereof. ROM 605 may act to communicate data and instructions uni-directionally to processor(s) 601, and RAM 604 may act to communicate data and instructions bi-directionally with processor(s) 601. ROM 605 and RAM 604 may include any suitable non-transitory, tangible computer-readable storage media.

In some instances, ROM 605 and RAM 604 include non-transitory, tangible computer-readable storage media for carrying out the method 590. In one example, a basic input/output system 606 (BIOS), including basic routines that help to transfer information between elements within computer system 600, such as during start-up, may be stored in the memory 603.

Fixed storage 608 is connected hi-directionally to processor(s) 601, optionally through storage control unit 607. Fixed storage 608 provides additional data storage capacity and may also include any suitable non-transitory, tangible computer-readable media described herein. Storage 608 may be used to store operating system 609, EXECS 610 (executables), data 611, API applications 612 (application programs/interfaces), and the like. Often, although not always, storage 608 is a secondary storage medium (such as a hard disk) that is slower than primary storage (e.g., memory 603). Storage 608 can also include an optical disk drive, a solid-state memory device (e.g., flash-based systems), or a combination of any of the above. Information in storage 608 may, in appropriate cases, be incorporated as virtual memory in memory 603.

In one example, storage device(s) 635 may be removably interfaced with computer system 600 (e.g., via an external port connector (not shown)) via a storage device interface 625. Particularly, storage device(s) 635 and an associated machine-readable medium may provide nonvolatile and/or volatile storage of machine-readable instructions, data structures, program modules, and/or other data for the computer system 600. In one example, software may reside, completely or partially, within a machine-readable medium on storage device(s) 635. In another example, software may reside, completely or partially, within processor(s) 601.

Bus 640 connects a wide variety of subsystems. Herein, reference to a bus may encompass one or more digital signal lines serving a common function, where appropriate. Bus 640 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 600 may also include an input device 633. In one example, a user of computer system 600 may enter commands and/or other information into computer system 600 via input device(s) 633. Examples of an input device(s) 633 include, but are not limited to, an alpha-numeric input device (e.g., a keyboard), a pointing device (e.g., a mouse or touchpad), a touchpad, a joystick, a gamepad, an audio input device (e.g., a microphone, a voice response system, etc.), an optical scanner, a video or still image capture device (e.g., a camera), and any combinations thereof. Input device(s) 633 may be interfaced to bus 640 via any of a variety of input interfaces 623 (e.g., input interface 623) including, but not limited to, serial, parallel, game port, USB, FIREWIRE, THUNDERBOLT, or any combination of the above.

In particular embodiments, when computer system 600 is connected to network 630, computer system 600 may communicate with other devices, such as mobile devices and enterprise systems, connected to network 630. Communications to and from computer system 600 may be sent through network interface 620. For example, network interface 620 may receive incoming communications (such as requests or responses from other devices) in the form of one or more packets (such as Internet Protocol (IP) packets) from network 630, and computer system 600 may store the incoming communications in memory 603 for processing. Computer system 600 may similarly store outgoing communications (such as requests or responses to other devices) in the form of one or more packets in memory 603 and communicated to network 630 from network interface 620. Processor(s) 601 may access these communication packets stored in memory 603 for processing.

Examples of the network interface 620 include, but are not limited to, a network interface card, a modem, and any combination thereof. Examples of a network 630 or network segment 630 include, but are not limited to, a wide area network (WAN) (e.g., the Internet, an enter rise network), a local area network (LAN) (e.g., a network associated with an office, a building, a campus or other relatively small geographic space), a telephone network, a direct connection between two computing devices, and any combinations thereof. A network, such as network 630, may employ a wired and/or a wireless mode of communication. In general, any network topology may be used.

Information and data can be displayed through a display 632. Examples of a display 632 include, but are not limited to, a liquid crystal display (LCD), an organic liquid crystal display (OLED), a cathode ray tube (CRT), a plasma display, and any combinations thereof. The display 632 can interface to the processor(s) 601, memory 603, and fixed storage 608, as well as other devices, such as input device(s) 633, via the bus 640. The display 632 is linked to the bus 640 via a video interface 622, and transport of data between the display 632 and the bus 640 can be controlled via the graphics control 621.

In addition to a display 632, computer system 600 may include one or more other peripheral output devices 634 including, but not limited to, an audio speaker, a printer, and any combinations thereof. Such peripheral output devices may be connected to the bus 640 via an output interface 624. Examples of an output interface 624 include, but are not limited to, a serial port, a parallel connection, a USB port, a FIREWIRE port, a THUNDERBOLT port, and any combinations thereof.

In addition or as an alternative, computer system 600 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a non-transitory, tangible computer-readable medium may encompass a circuit (such as an IC) storing software for execution, a circuit embodying logic for execution, or both, where appropriate. The present disclosure encompasses any suitable combination of hardware, software, or both.

Those of skill in the art will understand that information and signals may be represented using any of a variety of different technologies and techniques. Those of skill will further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in term of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

One or more steps of a method or algorithm described in connection with the embodiments disclosed herein (e.g., the method 590) may be embodied directly in hardware, in a software module executed by a processor, a software module implemented as digital logic devices, or in a combination of these. A software module may reside in RAM memory, flash memory, ROM memory, EPROM memory, EEPROM memory, registers, hard disk, a removable disk, a CD-ROM, or any other form of non-transitory, tangible computer-readable storage medium to own in the art. An exemplary non-transitory, tangible computer-readable storage medium is coupled to the processor such that the processor can read information from, and write information to, the non-transitory, tangible computer-readable storage medium. In the alternative, the non-transitory, tangible computer-readable storage medium may be integral to the processor. The processor and the non-transitory, tangible computer-readable storage medium may reside in an ASIC. The ASIC may reside in a user terminal. In the alternative, the processor and the non-transitory, tangible computer-readable storage medium may reside as discrete components in a user terminal. In some embodiments, a software module may be implemented as digital logic components such as those in an FPGA once programmed with the software module.

Figure 7:
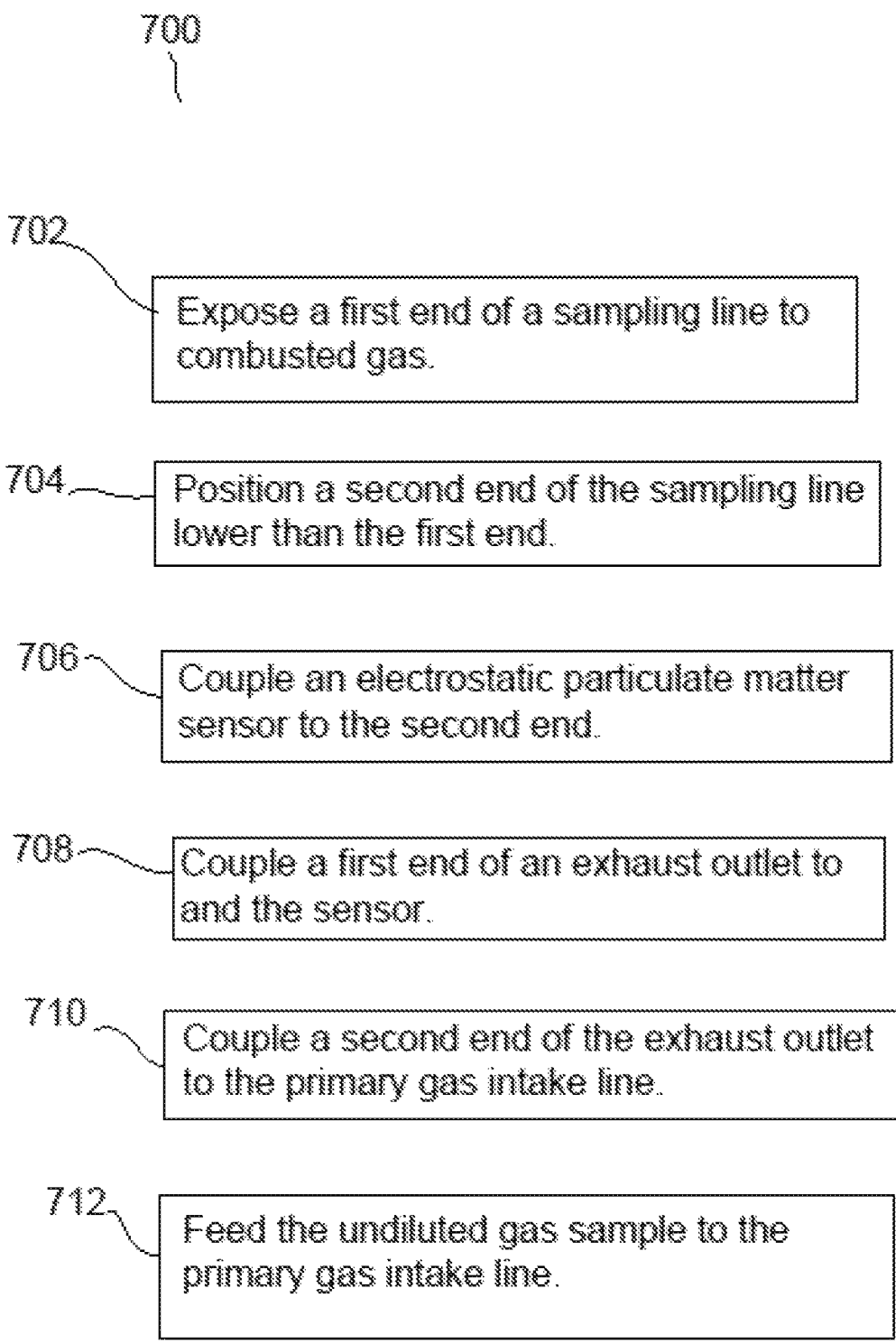
FIG. 7 depicts a diagrammatic representation of a method of retrofitting an oil or gas facility.

Turning now to FIG. 7, a method 700 of retrofitting is now described.

The method 700 may include a method of retrofitting an enclosed combustion device stack with an emissions detection system, the enclosed combustion device stack having a lower portion with an enclosed combustion device stack burner and a primary gas intake line, and an upper portion with a stack exit port.

The method 700 may include exposing 702 a first end of a sampling line to combusted gas passing through the stack exit port, the sampling line configured to receive an undiluted gas sample from the stack exit port.

The method 700 may include positioning 704 a second end of the sampling line lower than the first end.

The method 700 may include coupling 706 an electrostatic particulate matter sensor to the second end of the sampling line, the second end downstream of the first end, the electrostatic particulate matter sensor positioned and configured to analyze the undiluted gas sample;

The method 700 may include coupling 708 a first end of an exhaust outlet to and downstream of the electrostatic particulate matter sensor, the exhaust outlet port configured to receive the undiluted gas sample from the electrostatic particulate matter sensor;

The method 700 may include coupling 710 a second end of the exhaust outlet to the primary gas intake line upstream of the enclosed combustion device stack burner; and The method 700 may include feeding 712 the undiluted gas sample to the primary gas intake line.

Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

The invention claimed is:

1. An emission detection system for an enclosed combustion device stack having a lower portion with an enclosed combustion device stack burner and a primary gas intake line, and an upper portion with a stack exit port, the detection system comprising:
   a sampling line having a first end exposed to a combusted gas passing through the stack exit port, the sampling line configured to receive an undiluted gas sample from the stack exit port;
   an electrostatic particulate matter sensor coupled to a second end of the sampling line, the second end positioned lower than and downstream of the first end, the electrostatic particulate matter sensor positioned and configured to analyze the undiluted gas sample; and
   an exhaust outlet coupled to and downstream of the electrostatic particulate matter sensor, the exhaust outlet configured to receive the undiluted gas sample from the electrostatic particulate matter sensor and feed the undiluted gas sample to the primary gas intake line upstream of the enclosed combustion device stack burner; wherein
   the combusted gas comprises a first pressure;
   the primary gas intake line comprises primary gas at a second pressure different from the first pressure; and
   the sampling line, the electrostatic particulate matter sensor, the second pressure, and the exhaust outlet are configured to passively move the undiluted gas sample from the stack exit port to the electrostatic particulate matter sensor.

2. The system of claim 1, wherein:
   the sampling line has a length selected to provide a temperature differential between the first end and the second end, the temperature differential selected to prevent damage to the electrostatic particulate matter sensor.

3. The system of claim 1, wherein:
   the electrostatic particulate matter sensor is configured to emit a signal if the electrostatic particulate matter sensor determines the undiluted gas sample has a particulate value that exceeds a particulate threshold value.

4. A method of retrofitting an enclosed combustion device stack with an emissions detection system, the enclosed combustion device stack having a lower portion with an enclosed combustion device stack burner and a primary gas intake line, and an upper portion with a stack exit port, the method comprising:
   exposing a first end of a sampling line to combusted gas passing through the stack exit port, the sampling line configured to receive an undiluted gas sample from the stack exit port;
   positioning a second end of the sampling line lower than the first end;
   coupling an electrostatic particulate matter sensor to the second end of the sampling line, the second end downstream of the first end, the electrostatic particulate matter sensor positioned and configured to analyze the undiluted gas sample;
   coupling a first end of an exhaust outlet to and downstream of the electrostatic particulate matter sensor, the exhaust outlet port configured to receive the undiluted gas sample from the electrostatic particulate matter sensor;
   coupling a second end of the exhaust outlet to the primary gas intake line upstream of the enclosed combustion device stack burner; and
   feeding the undiluted gas sample to the primary gas intake line; wherein
   the combusted gas comprises a first pressure;
   the primary gas intake line comprises primary gas at a second pressure different from the first pressure; and
   the sampling line, the electrostatic particulate matter sensor, the second pressure, and the exhaust outlet are configured to passively move the undiluted gas sample from the stack exit port to the electrostatic particulate matter sensor.

5. The method of claim 4, wherein:
   the sampling line has a length selected to provide a temperature differential between the first end and the second end, the temperature differential selected to prevent damage to the electrostatic particulate matter sensor.

6. The method of claim 4, wherein:
   the electrostatic particulate matter sensor is configured to emit a signal if the electrostatic particulate matter sensor determines the undiluted gas sample has a particulate value that exceeds a particulate threshold value.

7. An oil or gas facility comprising:
   an enclosed combustion device stack having a lower portion with an enclosed combustion device stack burner and a primary gas intake line, and an upper portion with a stack exit port; and
   an emissions detection system, the emissions detection system having:
   (a) a sampling line having a first end exposed to a combusted gas passing through the stack exit port, the sampling line configured to receive an undiluted gas sample from the stack exit port;

(b) an electrostatic particulate matter sensor coupled to a second end of the sampling line, the second end positioned lower than and downstream of the first end, the electrostatic particulate matter sensor positioned and configured to analyze the undiluted gas sample; and (c) an exhaust outlet coupled to and downstream of the electrostatic particulate matter sensor, the exhaust outlet port configured to receive the undiluted gas sample from the electrostatic particulate matter sensor and feed the undiluted gas sample to the primary gas intake line upstream of the enclosed combustion device stack burner; wherein the combusted gas comprises a first pressure;

the primary gas intake line comprises primary gas at a second pressure different from the first pressure; and the sampling line, the electrostatic particulate matter sensor, the second pressure, and the exhaust outlet are configured to passively move the undiluted gas sample from the stack exit port to the electrostatic particulate matter sensor.

8. The facility of claim 7, wherein:

the sampling line has a length selected to provide a temperature differential between the first end and the second end, the temperature differential selected to prevent damage to the electrostatic particulate matter sensor.

9. The facility of claim 7, wherein:

the emissions detection system is a retrofitted emissions detection system.

10. The facility of claim 7, wherein:

the electrostatic particulate matter sensor is configured to emit a signal if the electrostatic particulate matter sensor determines the undiluted gas sample has a particulate value that exceeds a particulate threshold value.

* * * * *